(12) United States Patent
Weijand

(10) Patent No.: US 6,298,271 B1
(45) Date of Patent: Oct. 2, 2001

(54) MEDICAL SYSTEM HAVING IMPROVED TELEMETRY

(75) Inventor: Koen J Weijand, Rockanje (NL)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/356,340

(22) Filed: Jul. 19, 1999

(51) Int. Cl.[7] .................................................... A61N 1/37
(52) U.S. Cl. ................................................................ 607/60
(58) Field of Search .......................... 600/510; 128/903; 607/32, 60

(56) References Cited

U.S. PATENT DOCUMENTS

| | | |
|---|---|---|
| 4,542,532 | 9/1985 | McQuilkin ............................. 455/78 |
| 5,168,871 | 12/1992 | Grevious ............................... 128/419 |
| 5,630,835 * | 5/1997 | Brownlee ............................... 607/60 |
| 5,674,265 * | 10/1997 | Deschamps et al. ................... 607/60 |

* cited by examiner

Primary Examiner—William E. Kamm
(74) Attorney, Agent, or Firm—Beth L. McMahon

(57) ABSTRACT

A medical system having improved telemetry, the medical system featuring a programmer having a programming head. The system provides improved telemetry due to the unique antenna scheme within the programmer head. The antenna scheme utilizes a first antenna and a second antenna, the antennas disposed in a concentric and co-planar manner. This concentric and co-planar disposition permits the programmer head to be of much smaller and, thus, a more portable size than was previously possible. The antenna is further coupled with circuitry or software or both to reduce far field response (noise). The antenna may be constructed using printed circuit board, and thus be integrated with circuitry.

19 Claims, 8 Drawing Sheets

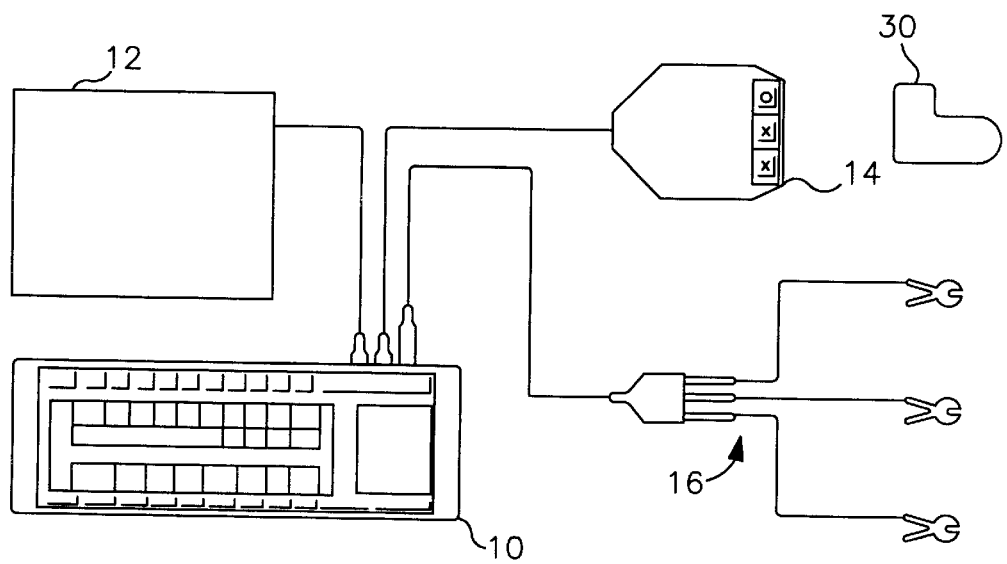
FIG. IA
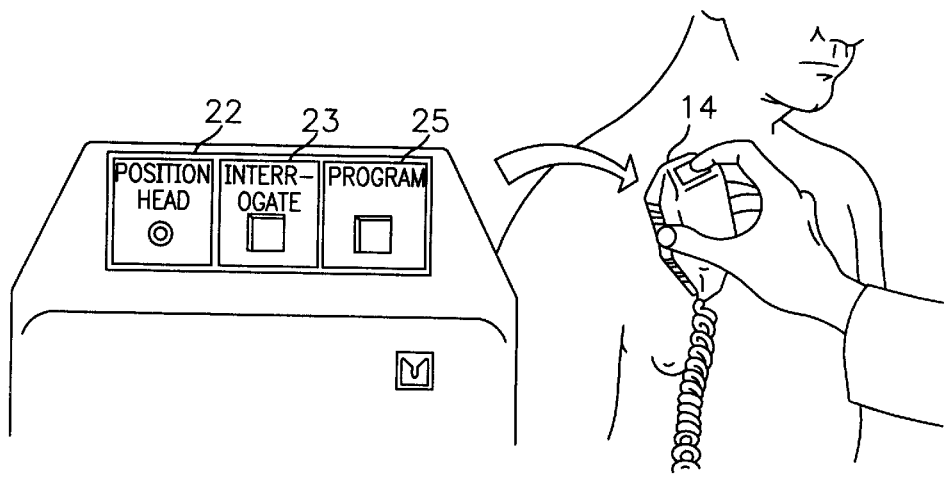
FIG. IB
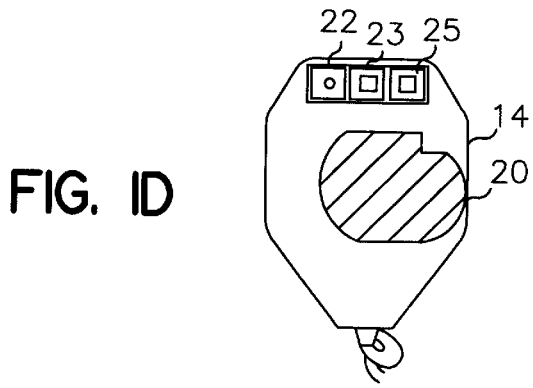
FIG. ID

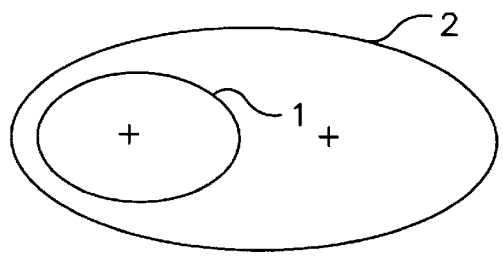
FIG. 7A — Oval & offset + Planar
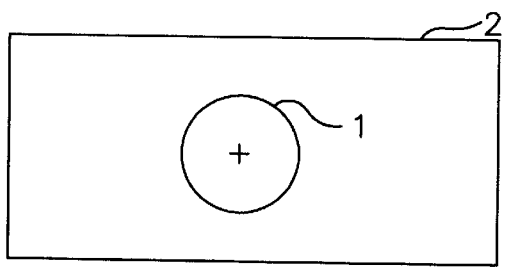
FIG. 7B — Square & Circle + Planar
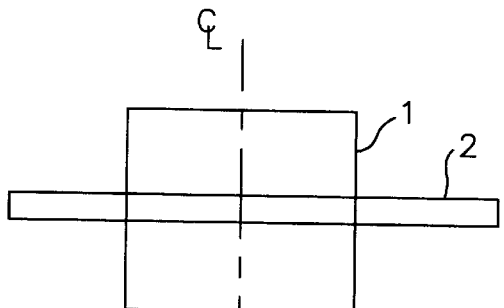
FIG. 7C — Planar & Coaxial but with different thickness
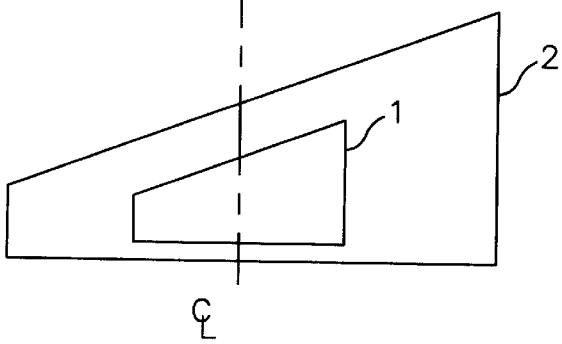
FIG. 7D — Coaxial & Planar but ramped
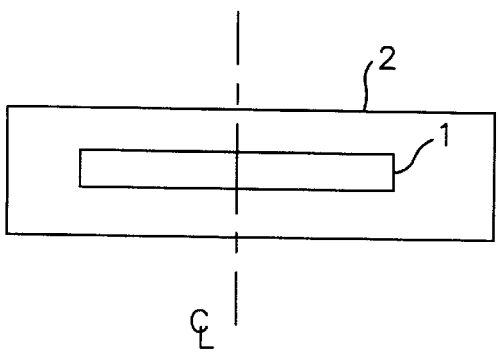
FIG. 7E — Planar & Coaxial but with outer thicker than inner

MEDICAL SYSTEM HAVING IMPROVED TELEMETRY

FIELD OF THE INVENTION

The invention relates generally to system having two-way communication between devices. More specifically, the invention relates to external transceivers which remotely communicate with implanted medical devices. Part of this two-way communication link consists of control or programming signals transmitted from the external device to the implanted device for the purpose of altering the operation of the implanted device. The remainder of the link consists of low-level telemetry transmissions from the implant to the external device for the purpose of conveying information such as current status, battery level, or patient data.

BACKGROUND OF THE INVENTION

Two-way communication with implanted medical devices imposes special problems which become even more acute in an interference-prone environment, especially where the medical devices are essential to maintaining life functions. Necessarily, implanted medical devices require ultra-low power levels from long-lived batteries. The most common implanted telemetry system employs a single, multi-turned coil to externally receive the low-level telemetry signals. These single-coil, receiving antennas are quite susceptible to interference from electric, magnetic and electromagnetic field sources which are present in the clinical environment.

The present invention employs two noise-canceling, antenna coils, which improve the signal-to-noise ratio significantly, and a circuit which permits transmission and reception of signals through the same antenna coil network without interactive tuning problems and without the employment of any switching devices. The improved, external transceiver circuit permits two-way communications with implanted medical devices in close proximity (on the order of 4 inches to 2 feet) to common interference sources such as cathode ray tubes and video monitors. Moreover, because the antenna coils reside within the same plane and our preferably co-axial they require a minimum amount of volume, leading to a much smaller, more portable programmer head. Finally, a system featuring the present invention may be cheaper, due to the fact that the disclosed antenna may be constructed using printed circuit board, and thus be integrated with circuitry.

SUMMARY OF THE INVENTION

A medical system having improved telemetry, the medical system featuring a programmer having a programming head. The system provides improved telemetry due to the unique antenna scheme within the programmer head. The antenna scheme utilizes a first antenna and a second antenna, the antennas disposed in a concentric and co-planar manner. This concentric and co-planar disposition permits the programmer head to be of much smaller and, thus, a more portable size than was previously possible. The antenna is further coupled with circuitry or software or both to reduce far field response (noise). The antenna may be constructed using printed circuit board, and thus be integrated with circuitry.

BRIEF DESCRIPTION OF THE DRAWINGS

FIG. 1A depicts the general configuration of a programmer in which the present invention may be used.

FIG. 1B is a detailed view of programmer head 14.

FIG. 1D is a detailed view of programmer head 14 and in particular illustrates the transmitting and receiving components 20 found within the head and the particular subject of the present invention.

FIG. 7 depicts an alternative embodiment for providing coils according to the present invention.

Figure 1C:
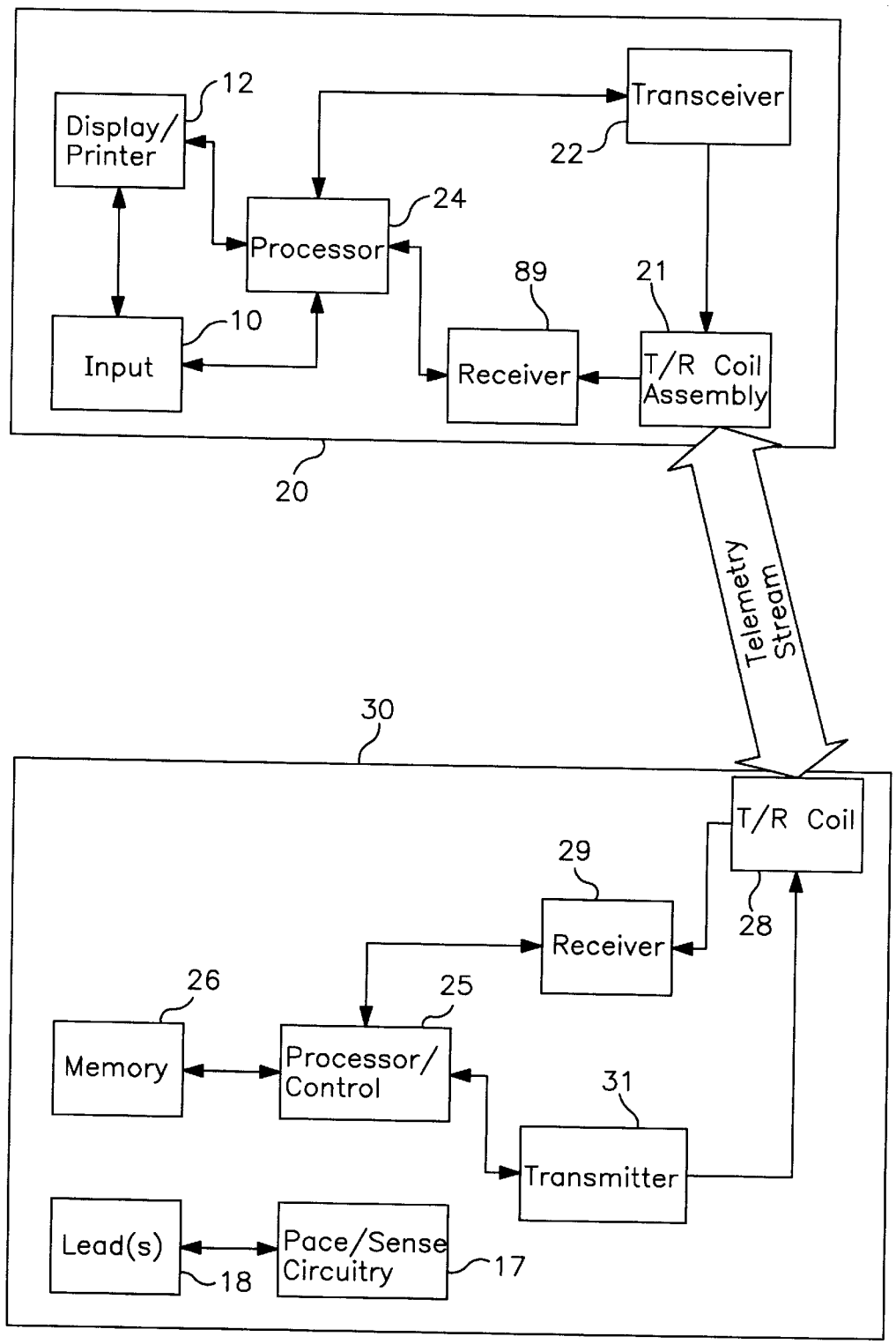
FIG. 1C shows a block diagram of a system incorporating the telemetry receiver of this invention.

The FIGS. are not necessarily to scale.

DESCRIPTION OF THE PREFERRED EMBODIMENTS

FIG. 1A depicts the general configuration of a programmer in which the present invention may be used. Typical programmer currently used, such as the Medtronic™ model 9790 programmer feature a keyboard 10 and display 12. A series of one or more leads 16 are provided to provide direct electrical coupling to the patient, e.g. to collect ECG signals. Finally, a programmer head 14 is provided. This head transmits and receives signal through which the programmer may communicate with an implanted device 30. In the present system head 14 transmits and receives RF signals.

FIG. 1B is a detailed view of programmer head 14. As seen head 14 possesses a pair of push button switches 23 and 25 labeled INTERROGATE and PROGRAM respectively. In use, the physician depresses one or the other of the two buttons to initiate a series of communications with an implanted device. Also commonly provided on programming heads 14 is a light 22 to indicate the position of the head relative to the implanted device. That is the light may illuminate or change color depending upon the proximity of the head to an implanted device.

Referring now to FIG. 1C, there is shown a block diagram of a system incorporating the telemetry receiver of this invention. While the invention is described in the context of an external device which receives telemetry signals from an implanted medical device, the invention is not limited to the environment of medical devices.

An external device, such as a programmer used in cardiac pacing systems, is illustrated at 20. The device picks up data at t/r coil 21, which data has been telemetered from another device illustrated at 30, e.g., an implanted cardiac pacemaker. The data which is uplinked to device 20 is inputted to processor block 24 via receiver 89, where it may be stored, analyzed, etc. The data can be displayed by any suitable display or printer, as shown at 15. Such programmer devices also have input capability, as by receiving tapes, discs, or data inputted by keyboard, as shown at 16. Device 30 also has a transmitter 22 for sending data to the implanted device 30. The portions of implanted device 30 that are important to this invention are illustrated within block 30. The transmitter 31 is controlled by block 25, and transmits encoded data through t/r coil 28 to the external device 20. In practice, the device 30 can also receive data from external device 20, through receiver 29 which is connected to processor 25. Processor 25 is also suitably used to control operation of pace sense circuits 17, which transmit pacing signals to a patient's heart through leads 18, and receive heart signals for processing. Block 25 suitably uses a microprocessor and associated memory 26, in a know fashion.

FIG. 1D is a detailed view of programmer head 14 and in particular illustrates the transmitting and receiving components 20 found within the head and the particular subject of the present invention. As mentioned above, programmers communicate with implanted devices through the transmission and reception of telemetry. Often this telemetry is carried on RF waves, which require the provision of appropriately configured antennas in the programming head 14.

Figure 2:
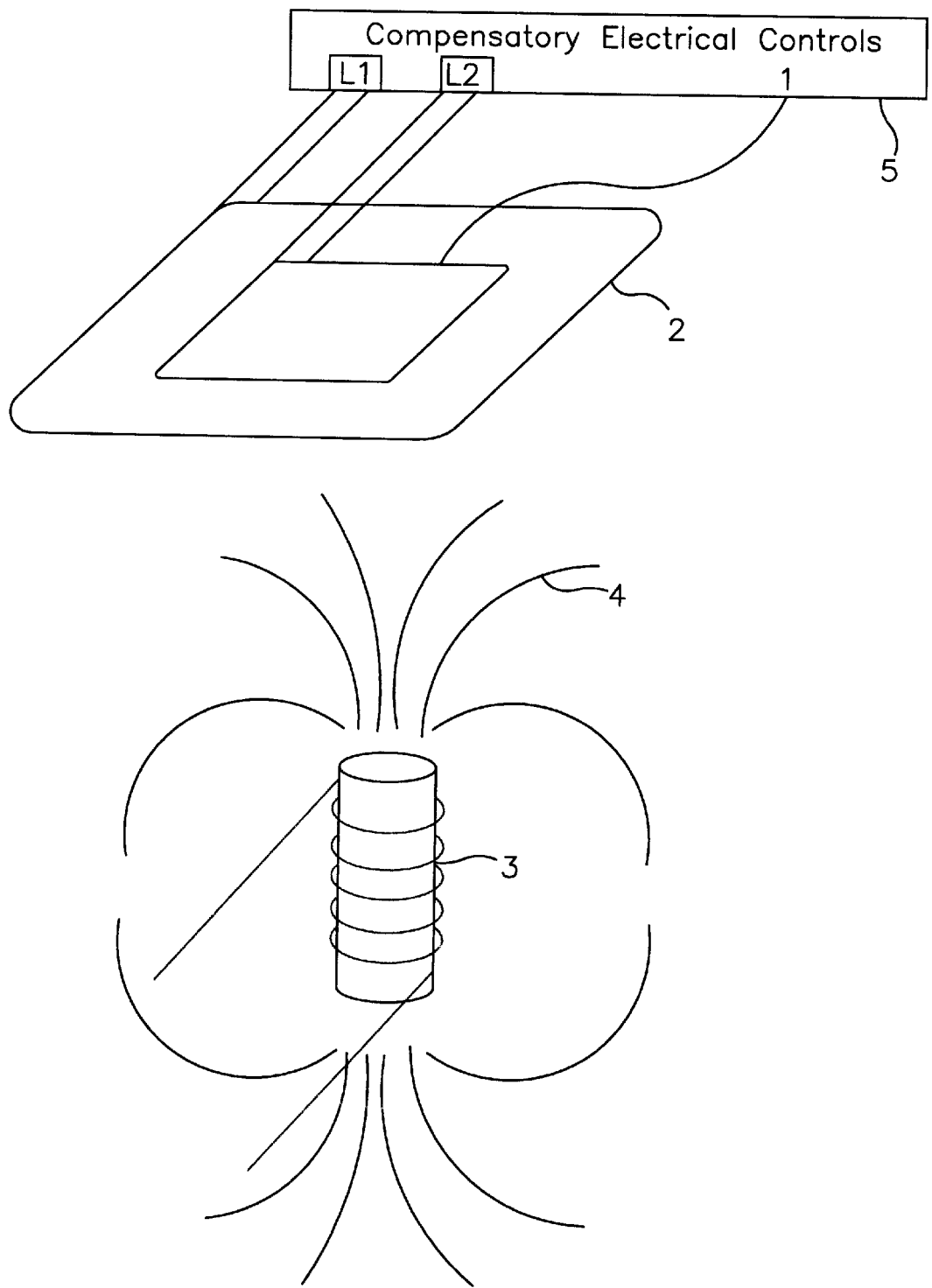
FIG. 2 depicts the relation between the antenna coils 1 and 2 which would be within programming head 14 according to the present invention as they would relate to the transmitting antenna 3 from an implanted device.

FIG. 2 depicts the relation between the antenna coils 1 and 2 which would be within programming head 14 according to the present invention as they would relate to the transmitting antenna 3 from an implanted device. As seen, the transmitting antenna 3 creates a field depicted here with a variety of flux lines, generally 4. The coils 1 and 2 are in the same plane but do not have the same size. Moreover, these coils need not even have the same number of windings. Although shown as roughly square, coils may be in any appropriate shape, as discussed below more fully with regards to FIG. 9. As shown, coils 1 and 2 are coupled to compensatory electrical controls to provide the far field noise canceling effect. As can be appreciated, the different sizes of coils 1 and 2 result in a different pick up of the magnetic flux of the field and, thus, induces different voltages in each of the coils. These different voltages may be compensated for by the compensatory electrical controls to thus achieve far field noise canceling effect.

Figure 3A:
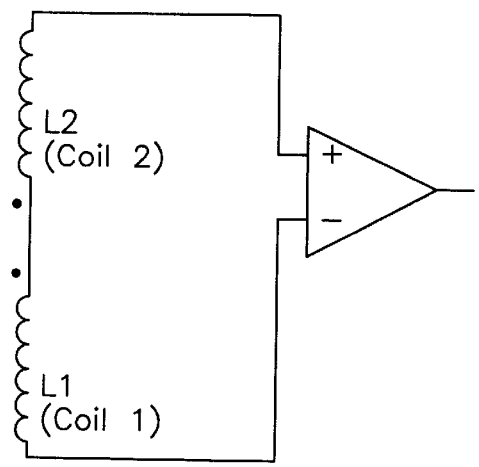
FIGS. 3A–3C each disclose compensatory electrical controls which may be used to provide the desired far field cancellation result.
Figure 3B:
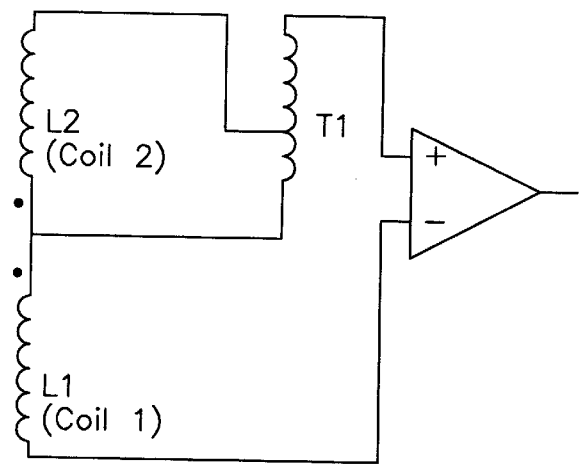
Figure 3C:
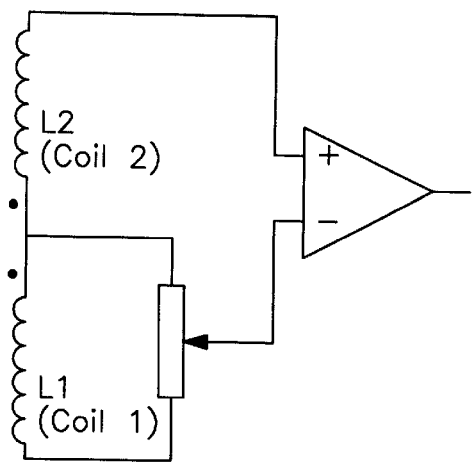

FIGS. 3A–3C each disclose compensatory electrical controls which may be used to provide the desired far field cancellation result. Generally speaking, the voltage generated by a coil is linearly related to the number of turns and the area of the coil (assuming, for simplicity, a far field source which gives uniform magnetic flux per unit area.) Thus the more turns in a coil, or the larger the coil, the more voltage created. From this, we have found that coils of non-equal area can be compensated for by varying the number of windings in each. FIG. 3A is particularly beneficial when the inner coil antenna L1 is smaller than outer coil L2 and inner coil L1 has more turns or windings to as to generate the same voltage for far fields, but in opposite phase. For example, a typical set of coils would have the following characteristics: The outer coil L2 would be circular and be six square inches in area and have 25 turns while the inner coil L1 would be on quarter the area, or one and one-half (1.5) square inches and have 100 turns.

FIG. 3B shows an alternative embodiment for providing far field cancellation. In particular, this embodiment features the step-up transformer T1 which may be used to compensate for the small area of coil 2. This use of a step-up transformer is particularly believed useful if the voltage loss cannot be made up for by providing coil 2 with more turns. Recall, the voltage induced in the coils by the field is a function of both the coil geometry as well as the number of turns in the coils. Thus the compensatory electrical control scheme used in the invention depends both upon the size of the coils as well as the number of turns used in each coil. Other factors which affect the ultimate design of a programmer head include, among other things, the carrier frequency, transmission power.

FIG. 3C shows an alternative embodiment for providing the compensatory electrical controls. In particular, this embodiment approaches the desired far field noise canceling effect in a manner opposite to that shown in FIG. 3B. In particular, in this design, rather than stepping up the output from coil L2 the output from coil L1 is attenuated.

Figure 4A:
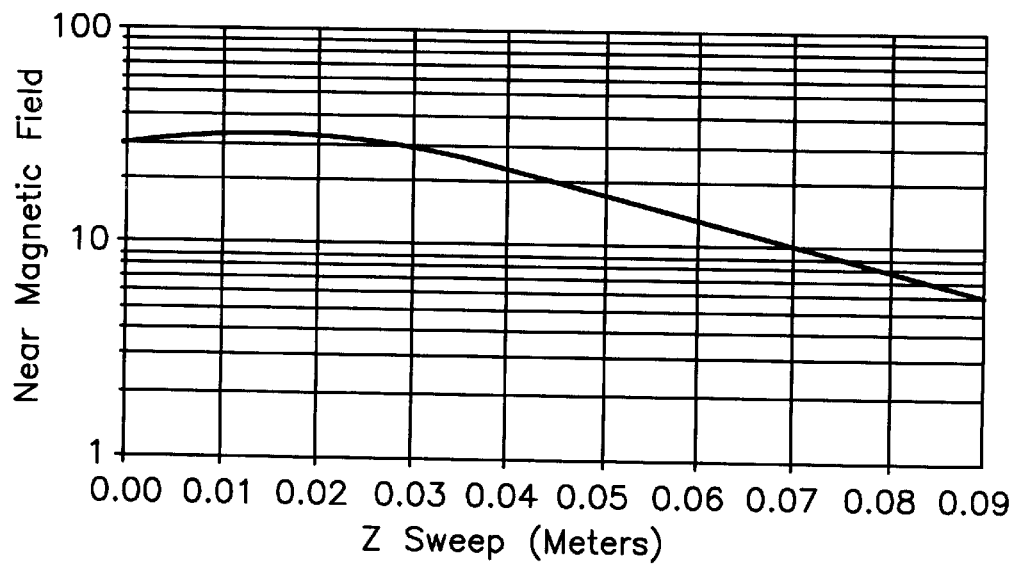
FIG. 4A shows the response of a single loop receiving antenna as a function of the distance to a transmitter and FIG. 4B shows the response of a dual loop receiving antenna as a function of the distance to a transmitter.
Figure 4B:
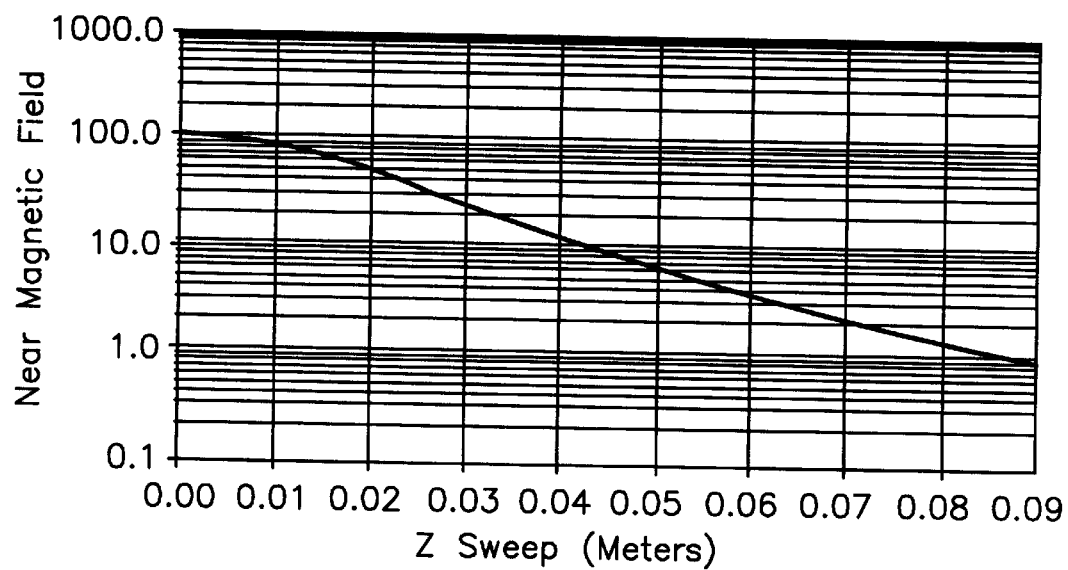

FIG. 4A shows the response of a prior art single loop receiving antenna as a function of the distance to a transmitter and FIG. 4B shows the response of a dual loop receiving antenna according to the present invention as a function of the distance to a transmitter. As can be seen in a comparison of these FIGS, a dual coil, concentric co-planar antenna of the present invention provides superior performance compared to a single coil version. This is seen specifically in FIG. 4A, where a single coil has a gain of 30 versus FIG. 4B, where a dual coil antenna has a gain of 100, both being 0.00 meters distance (Z).

Figure 5:
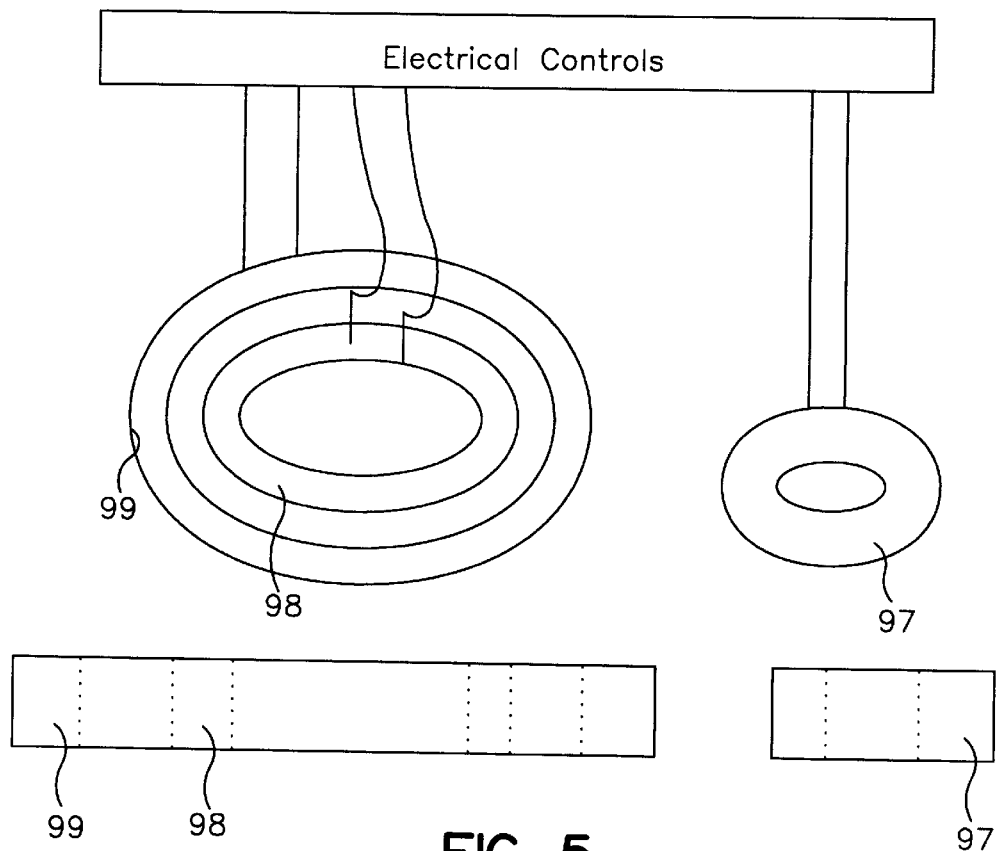
FIG. 5 shows an alternative embodiment of the present invention.

FIG. 5 shows an alternative embodiment of the present invention. In this embodiment a further third coil 97 is provided alongside and in the same plane as a co-planar and co-axial coil design 98, 99 as previously described above. In addition, third coil 97, besides being provided alongside and in the same plane as a co-planar and co-axial coil design 98, 99, could also be provided co-planar and co-axial to coil 98, 99 instead of alongside. In this last configuration there would be a tri-coil array in a single plane and all of which would be concentric. The additional third coil may be used to accommodate rotated uplink fields. This additional coil will be switched in, instead of the inner coil, upon such occurrence. Through this structure there is a butterfly type receiving type structure. It should be pointed out, this design does have a disadvantage to the concentric design in that it has two optimal positions and it does have a null output depending upon the rotation along the Z axis. Despite these limitations the additional third co-planar coil provides greater freedom in trading of far field, close field responses. The range of such structure, however, will be limited, as the turn's ratios cannot be very large.

Figure 6A:
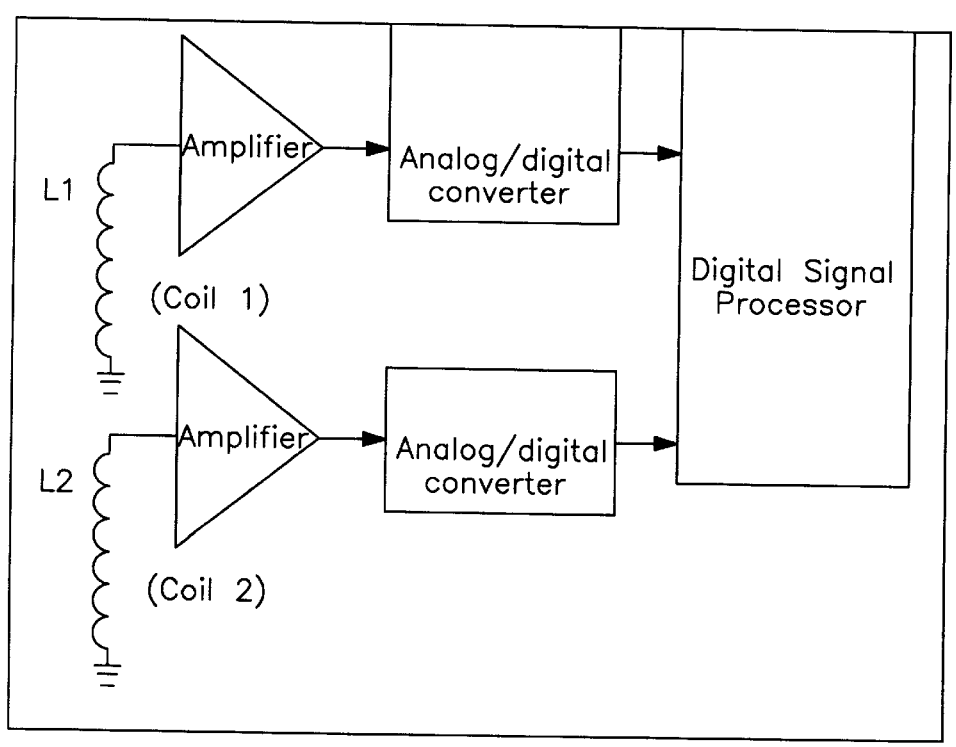
FIGS. 6A and 6B show an alternative means for providing far field noise-canceling effects.
Figure 6B:
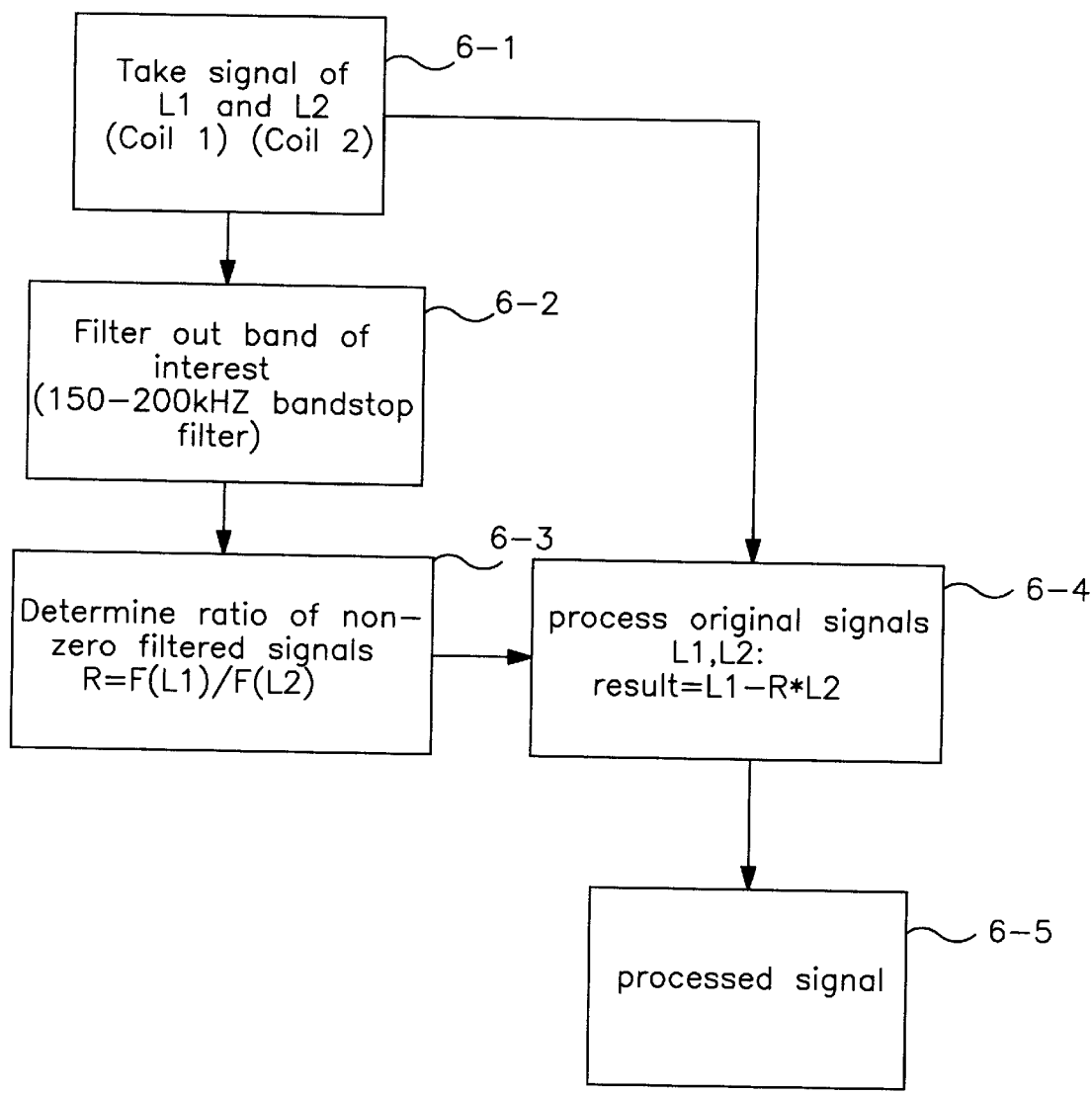

FIGS. 6A and 6B shows an alternative means for providing far field noise-canceling effects. In particular, FIG. 6A shows a structure in which two coils may have their signals processed within their digital domain. Coils L1, L2 (coil 1 and coil 2) are disposed in a co-planar, co-axial manner, as already described above. As seen, each coil itself is coupled through an amplifier to an analog/digital converter. Thereafter the digital signals of each coil are processed using a digital signal processor, as shown.

FIG. 6B shows the steps used to process the signals gathered by the structure in FIG. 6A. As seen, the signals are received or taken from coil 1 and coil 2 at 6-1. Thereafter, at 6-2 signals outside the band of telemetry frequencies are removed and the ratio of non-zero filtered signals is performed at 6-3. At 6-4 the result of the operation in 6-3 is processed along side the original sent signals from 6-1 so as to achieve the appropriate far field noise suppression, depicted here as processed signal at 6-5.

FIG. 7 depicts an alternative embodiment for providing coils according to the present invention. While the invention disclosed above is preferably practiced using congruent coil shapes which are disposed co-axially, in a particular environment the invention may also be practiced using non-congruent or non co-axial or both coils. Examples of such coils are shown in FIGS. 7A–7E.

FIG. 7A depicts a scheme in which dual oval coils are set in a non co-axial disposition.

FIG. 7B shows co-axial disposition of a square outer coil and circular inner coil. In both FIGS. 7A and 7B the coils are set in a planar configuration.

In FIG. 7C the coils are set in a manner in which they have different or varying thicknesses. In this configuration they would be co-planar and, indeed, they could even be congruent, although not necessarily. While depicted as co-axial it could also be imagined they could be in a non co-axial configuration.

FIG. 7D depicts an alternative embodiment in which the coils are co-axial and planar but which have a ramped or increasing thickness within the plane.

Finally, FIG. 7E depicts an embodiment in which the coils are disposed in a co-planar, co-axial configuration but with the outer coil having a greater thickness than the inner coil. It should be understood, as discussed above, that the windings of each coil may be suitably selected to obtain the desired output signals for the environment in which the antenna is to operate. Thus, the present invention has been described within the context of a medical system programmer. It should be understood, however, that the antenna of the present invention is not limited merely to medical systems but could congruently be used in other applications as well, such as in a variety of wireless devices.

What is claimed is:

1. A medical system having improved telemetry comprising:
   a first antenna in a first plane;
   a second antenna in the first plane; and
   the first and the second antenna coupled to means for reducing far field response (noise).

2. The system according to claim 1 further comprising the first antenna having a first lumen, and the second antenna positioned within first lumen.

3. The system according to claim 1 further comprising a third antenna, wherein the third antenna being coupled to means for reducing far field response.

4. The system according to claim 1 wherein the first antenna is circular in the first plane.

5. The system according to claim 1 wherein the first antenna is polygonal in the first plane.

6. The system according to claim 1 wherein the first antenna and the second antenna are coaxial.

7. The system according to claim 6 wherein the first antenna is circular in the first plane.

8. The system according to claim 6 wherein the first antenna is polygonal in the first plane.

9. The system according to claim 1 wherein the first antenna and the second antenna are non-coaxial.

10. The system according to claim 9 wherein the first antenna is circular in the first plane.

11. The system according to claim 9 wherein the first antenna is polygonal in the first plane.

12. The system according to claim 1 wherein first antenna includes a first number of turns.

13. The system according to claim 12 wherein the second antenna has a second number of turns.

14. The system according to claim 13 wherein the first number of turns is different than the second number of turns.

15. The system according to claim 1 further comprising means for providing therapy to a patient.

16. The system according to claim 15 wherein said means for providing therapy to a patient comprises means for providing electrical stimulation signals to the patient.

17. The system according to claim 16 wherein said means for providing therapy to a patient comprises means for providing drugs to the patient.

18. The system according to claim 1 further comprising means for monitoring a physiologic parameter of a patient.

19. The system according to claim 18 wherein the means for monitoring a physiologic parameter of a patient comprises means for monitoring a cardiac signal of the patient.

* * * * *